(12) United States Patent
McCawley

(10) Patent No.: US 8,062,260 B2
(45) Date of Patent: Nov. 22, 2011

(54) TROCAR CANNULA DEVICE WITH RETENTION FEATURE

(75) Inventor: Matthew D. McCawley, Costa Mesa, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 12/644,147

(22) Filed: Dec. 22, 2009

(65) Prior Publication Data
US 2011/0152773 A1 Jun. 23, 2011

(51) Int. Cl.
*A61M 5/178* (2006.01)
(52) U.S. Cl. .................. 604/164.12; 604/178; 604/294; 604/164.01; 606/4; 606/167
(58) Field of Classification Search .............. 604/21–22, 604/164.01, 164.12, 165.03, 178, 179, 264, 604/272, 289, 294; 606/4–6, 39, 45, 107, 606/108, 138, 167, 170
See application file for complete search history.

(56) References Cited

U.S. PATENT DOCUMENTS

| 4,963,147 | A | * | 10/1990 | Agee et al. | 606/170 |
|---|---|---|---|---|---|
| 5,997,560 | A | * | 12/1999 | Miller | 606/170 |
| 6,149,607 | A | * | 11/2000 | Simpson et al. | 600/567 |
| 6,551,291 | B1 | | 4/2003 | de Juan, Jr. et al. | |
| 6,638,233 | B2 | * | 10/2003 | Corvi et al. | 600/564 |
| 7,077,848 | B1 | | 7/2006 | de Juan, Jr. et al. | |
| 7,377,897 | B1 | * | 5/2008 | Kunkel et al. | 600/184 |
| 2006/0217655 | A1 | | 9/2006 | Vitullo et al. | |
| 2008/0172009 | A1 | * | 7/2008 | Attinger | 604/264 |
| 2008/0177239 | A1 | | 7/2008 | Li et al. | |

OTHER PUBLICATIONS

"ACCURUS® Surgical System 25-Gauge Instruments Portfolio," ALCON, Inc., 2005; 6 pgs.
Groves, N.; "More surgeons adopting 25-gauge vitrectomy technique," Ophthalmology Times; Jun. 2005; 5 pgs.
Groves, N.; "Tools for 25-gauge vitrectomy open door for other procedures," Ophthalmology Times; 30:12; Jun. 2005; 2 pgs.
Reimann, C.; "Expanding the Options for 25-ga. Vitrectomy," Review of Ophthalmology; Feb. 2005; 3 pgs.
Charters, L.; "Tackling complex retinal surgery possible with smaller instrumentation," Ophthalmology Times; 31:8; Apr. 2006; 1 pg.
Roe, R.H. et al.; "Small-Gauge Vitrectomy: The Future is Now," Rev. of Ophthalmology; 14:06; Jun. 1, 2007; 4 pgs.

* cited by examiner

*Primary Examiner* — Nicholas D. Lucchesi
*Assistant Examiner* — Quynh-Nhu H Vu
(74) *Attorney, Agent, or Firm* — W. David Lee

(57) ABSTRACT

A trocar cannula is disclosed. The trocar cannula comprises a cannula having at least one tab member formed therein. Each tab member is configured to provide a retention force between the cannula and tissue when the tab member is placed in a deformed position. The tab member is selectively moveable between a relaxed position, in which the cannula may be moved with respect to the tissue, and the deformed position, wherein the tab member frictionally engages the tissue.

17 Claims, 3 Drawing Sheets

TROCAR CANNULA DEVICE WITH RETENTION FEATURE

TECHNICAL FIELD

The present disclosure generally pertains to microsurgical instruments. More particularly, but not by way of limitation, the present disclosure relates to microsurgical instruments used in posterior segment ophthalmic surgery.

BACKGROUND

Many microsurgical procedures require precision cutting and/or removal of various body tissues. For example, vitreoretinal surgery often requires the cutting, removal, dissection, delamination, coagulation, or other manipulation of delicate tissues such as the vitreous humor, traction bands, membranes, or the retina. The vitreous humor, or vitreous, is composed of numerous microscopic fibers that are often attached to the retina. Therefore, cutting, removal, or other manipulation of the vitreous must be done with great care to avoid traction on the retina, the separation of the retina from the choroid, a retinal tear, or, in the worst case, cutting and removal of the retina itself.

Microsurgical instruments, such as vitrectomy probes, fiber optic illuminators, infusion cannulas, aspiration probes, scissors, forceps, and lasers are typically utilized during vitreoretinal surgery. These devices are generally inserted through one or more surgical incisions in the sclera near the pars plana, which are called sclerotomies. To establish an entry through the sclera into the posterior segment of the eye, trocar cannulas are typically used. The trocar cannula generally serves as a pathway through which various microsurgical instruments may be delivered to the posterior segment of the eye.

Typically, a surgeon relies upon friction between an outer surface of the trocar cannula and the sclera of the eye to maintain the trocar cannula's position within the eye. However, during an exchange of the microsurgical instruments, there is a risk that the trocar cannula may be inadvertently moved, which may cause injury to the patient. To insure against inadvertent movement of the trocar cannula, in prior art systems a surgeon grasps a cannula hub with a pair of forceps during the instrument exchange to maintain the position of the trocar cannula. Such a practice requires an extra step in the surgical procedure, thereby increasing the length of surgery. In addition, this practice also requires an extra hand to hold the forceps. Therefore, a need remains for an improved retention mechanism for a trocar cannula.

BRIEF SUMMARY

A trocar cannula is disclosed. The trocar cannula comprises a cannula having a tab member formed therein. The tab member is configured to provide a retention force between the cannula and tissue when the tab member is placed in a deformed position. The tab member is selectively moveable between a relaxed position, in which the cannula may be moved with respect to the tissue, and the deformed position, wherein the tab member frictionally engages the tissue.

In one exemplary arrangement, the tab member is biased into the relaxed position, but may be selectively moved into the deformed position by introduction of a medical instrument into the cannula. Once in the deformed position, the tab member frictionally engages tissue to retain the cannula with respect to the tissue. Upon withdrawal of the medical instrument from the cannula, the tab member is automatically returned to the relaxed position whereby the cannula may be moved with respect to the tissue.

BRIEF DESCRIPTION OF THE DRAWINGS

Embodiments of the present disclosure will now by described by way of example in greater detail with reference to the attached figures, in which.

DETAILED DESCRIPTION

Figure 1:
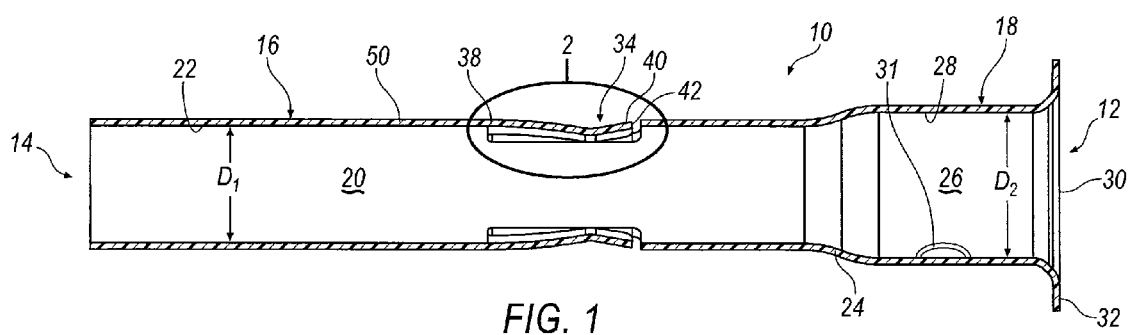
FIG. 1 is a cross-sectional view of an embodiment of a trocar cannula device.

Referring now to the discussion that follows and also to the drawings, illustrative approaches to the disclosed devices and methods are shown in detail. Although the drawings represent some possible approaches, the drawings are not necessarily to scale and certain features may be exaggerated, removed, or partially sectioned to better illustrate and explain the present disclosure. Further the descriptions set forth herein are not intended to be exhaustive or otherwise limit or restrict the claims to the precise forms and configurations shown in the drawings and disclosed in the following detailed description.

FIG. 1 illustrates an exemplary embodiment of a trocar cannula device 10. Trocar cannula device 10 is generally defined by an open proximal end 12 and an open distal end 14 and comprises a cannula section 16 and an introduction section 18. Cannula section 16 includes a generally hollow bore 20 defined by an internal surface 22. Cannula section 16 opens into introduction section 18. In one exemplary arrangement, a transition section 24 connects cannula section 16 to introduction section 18.

Introduction section 18 has a generally hollow chamber 26 defined by an internal surface 28 and an opening 30 positioned at proximal end 12. Surrounding opening 30 is an optional flange member 32. Internal surface 28 may optionally be configured with a protrusion 31 (shown in phantom in FIG. 1) that mates with a corresponding well (not shown) disposed on an external surface of 52. Details of protrusion 31 are discussed in commonly owned U.S. patent application Ser. No. 11/624,485, the contents of which are incorporated by reference in its entirety.

Cannula section 16 is defined by a first internal diameter $d_1$. Introduction section 18 is defined by a second internal diameter $D_2$. In one exemplary arrangement, first internal diameter $d_1$ is less than second internal diameter $D_2$. In one exemplary arrangement, trocar cannula device 10 is formed as a unitary member such that cannula section 16 and introduction section 18 are integrally connected together. Trocar cannula device 10 may be constructed from surgical stainless steel or other materials suitable for surgical applications.

Figure 8:
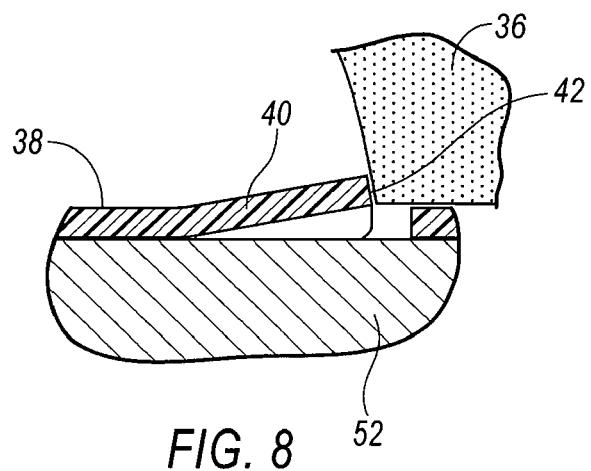
FIG. 8 is an enlarged cross-sectional view of a portion of the trocar cannula device and medical instrument of FIG. 3, with a retaining tab engaged with tissue.

As discussed above, during surgical procedures, trocar cannula device 10 is positioned within the patient's eye to provide a pathway for delivery of surgical instruments. To insure that trocar cannula device 10 is prevented from inadvertent dislodgement during a surgical procedure, trocar cannula device 10 is provided with at least one cantilever tab member 34. In some embodiments, such as that shown in the accompanying drawing figures, trocar cannula device 10 is provided with multiple cantilever tab members 34. Each cantilever tab member 34 is configured to increase a retention force required to remove trocar cannula device 10 from the sclera 36 (see FIG. 8) of the eye.

Figure 2:
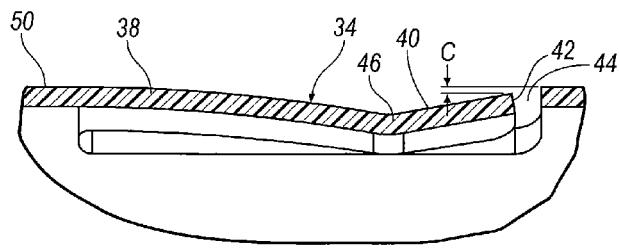
FIG. 2 is a is an enlarged cross-sectional view of area 2 of the trocar cannula device of FIG. 1.
Figure 4:
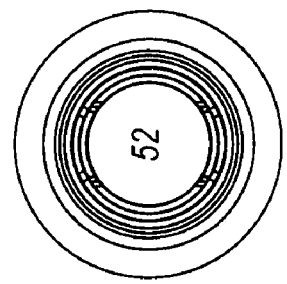
FIG. 4 is an end view of the trocar cannula device and medical instrument of FIG. 3.
Figure 3:
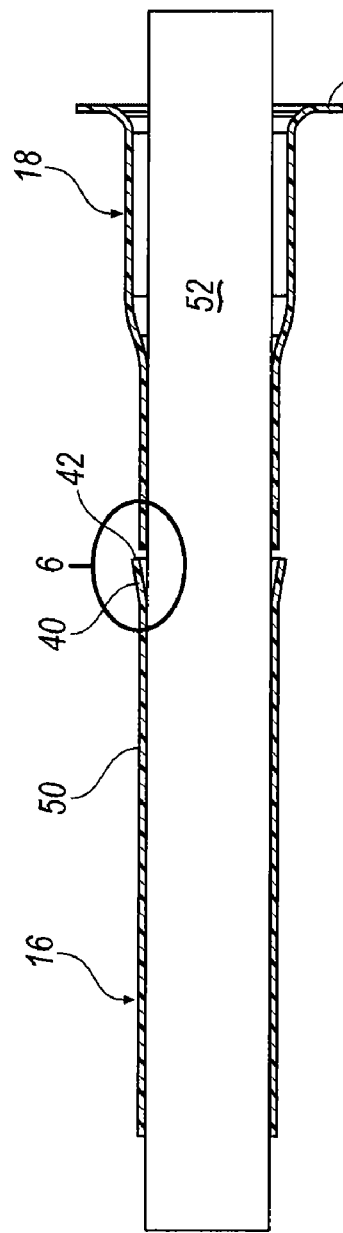
FIG. 3 is a cross-sectional view of the trocar cannula device of FIG. 1 with a medical instrument positioned therein.
Figure 5:
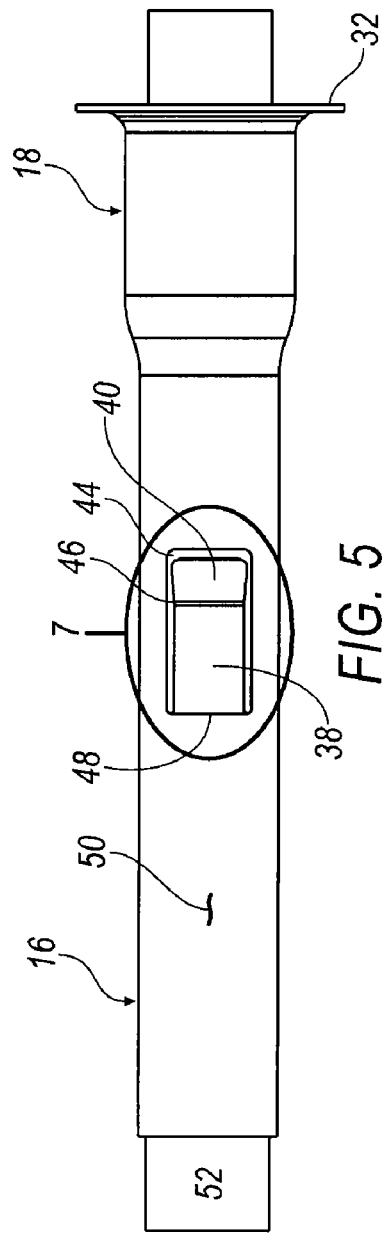
FIG. 5 is a top view of the trocar cannula device and medical instrument of FIG. 3.
Figure 6:
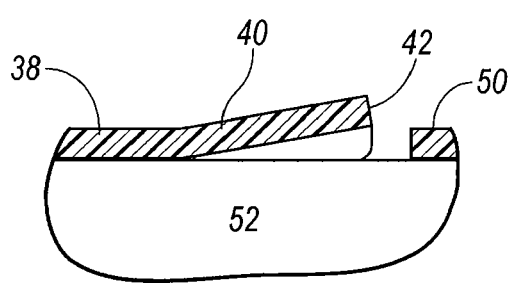
FIG. 6 is an enlarged cross-sectional view of area 6 of the trocar cannula device and medical instrument of FIG. 3.
Figure 7:
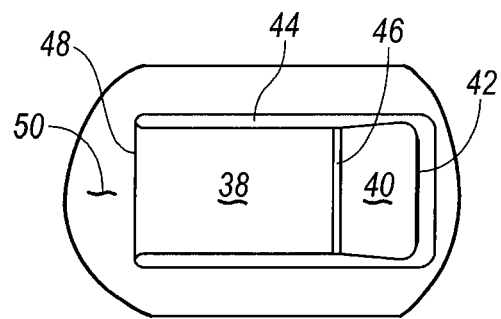
FIG. 7 is an enlarged top view of area 7 of the trocar cannula device of FIG. 5.

Details of cantilever tab member 34 will now be discussed. Cantilever tab member 34 is formed from a portion of a sidewall 38 of cannula section 16 and comprises a mechanical finger 40 that includes an upwardly biased end 42. Tab member 34 is formed by a generally U-shaped cut-out 44 that permits end 42 to move with respect to side wall 38. As seen in FIG. 2, cantilever tab member 34 includes a crimp section 46 that separates mechanical finger 40 from the portion of sidewall 38. Crimp section 46 is formed so as to pre-bias end 42 upwardly. Referring to FIG. 5, a bend area 48 is formed in sidewall 38. Bend area 48 is configured to bias cantilever tab member 34 inwardly with respect to an outside surface 50 by a predetermined distance when trocar cannula member 10 is in a relaxed state (best seen in FIG. 2). More specifically, in the relaxed state, cantilever tab member 34 (including biased end 42) sits below outer surface 50, thereby permitting trocar cannula member 10 to be easily moved with respect to sclera 36. In one embodiment, a slight clearance C is provided between an uppermost edge of biased end 42 and outside surface 50 (see FIG. 2).

However, referring now to FIGS. 3-8, when an instrument 52 is positioned within trocar cannula device 10, mechanical finger 40 is deflected outwardly from outside surface 50 in the radial direction such that biased end 42 extends outwardly from outside surface 50. More specifically, instrument 52 contacts crimp section 46 as it is inserted into bore 20, forcing crimp section 46 upwardly, and consequently forcing biased end 42 upward into a deformed position (seen best in FIGS. 6 and 8) such that biased end 42 may grip sclera 36. The radial deflection of mechanical finger 40 creates a mechanical mechanism for increasing the retention force between trocar cannula 10 and sclera 36 as compared to a simple frictional engagement of outside surface 50 of trocar cannula 10 and sclera 36. The added retention force from mechanical finger 40 eliminates the need to have the surgeon retain trocar cannula 10 with forceps or other means during an instrument exchange. The elimination of this step serves to reduce procedure time, as well as provide the surgeon with a free hand for handling additional instruments.

Once a procedure is complete, and all instruments are removed from trocar cannula device 10, cantilever tab member 34 automatically returns to the relaxed position whereby mechanical finger 40 (including biased end 42) is disposed below outer surface 50. The return feature is due to the configuration of bend area 48. Once in this position, trocar cannula device 10 may be easily removed from the patient.

In one exemplary arrangement, the instrument 52 is an infusion cannula that permits irrigating fluid to enter the posterior segment of the eye to maintain a suitable intraocular pressure. However, it is understood that other microsurgical instruments may also be used with trocar cannula device 10.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A trocar cannula, comprising:
a cannula defined by a distal end and a proximal end; and
at least one tab member formed from a portion of a sidewall of the cannula;
wherein each tab member is configured to provide a retention force between the cannula and tissue, wherein the tab member is selectively moveable between a relaxed position in which the cannula can be moved with respect to the tissue and a deformed position wherein the tab member frictionally engages the tissue, and wherein the tab member is recessed inwardly of an outer surface of the cannula when the tab member is in the relaxed position.

2. The trocar cannula of claim 1, wherein the tab member is deflected upwardly from the outside surface of the cannula when in the deformed position.

3. The trocar cannula of claim 1, wherein the tab member further comprises a mechanical finger having an upwardly biased end.

4. The trocar cannula of claim 3, further comprising a crimp section that serves to bias the biased end upwardly.

5. The trocar cannula of claim 3, wherein an uppermost edge of the biased end is positioned a predetermined distance below an outside surface of the cannula.

6. The trocar cannula of claim 1, wherein the tab member is formed by a generally U-shaped cut-out that permits an end of the tab member to move with respect to the sidewall of the cannula.

7. The trocar cannula of claim 6, further comprising a bend area formed in the sidewall that is configured to bias the tab member inwardly with respect to an outside surface of the cannula, into the relaxed position.

8. The trocar cannula of claim 7, wherein the bend area is configured to permit selective upward deflection of tab member, above the outside surface of the cannula, into the deformed position when an instrument is inserted into the cannula.

9. A trocar cannula system, comprising:
a cannula defined by a distal end and a proximal end; and
a medical instrument selectively insertable within the cannula;
wherein the cannula further comprises at least one tab member formed from a portion of a sidewall of the cannula, each tab member being configured to provide a retention force between the cannula and tissue when the medical instrument is inserted within the cannula;
wherein the tab member is recessed inwardly of an outer surface of the cannula when the tab member is in a relaxed position;
and wherein the tab member is selectively moveable between the relaxed position in which the cannula can be moved with respect to the tissue and a deformed position wherein the tab member frictionally engages the tissue.

10. The trocar cannula system of claim 9, wherein the tab member further comprises a mechanical finger having crimp section and a biased end, wherein the crimp section biases the biased end upwardly.

11. The trocar cannula system of claim 10, wherein an uppermost edge of the biased end is positioned below an outside surface of the cannula when the tab member is in the relaxed position.

12. The trocar cannula system of claim 11, wherein the instrument contacts the crimp section to force the biased end upwardly from the outside surface of the cannula when the tab member is in the deflected position.

13. The trocar cannula system of claim 9, wherein the tab member is configured to return to the relaxed position from the deflected position when the instrument is removed from the cannula.

14. The trocar cannula system of claim 9, wherein the tab member is formed by a generally U-shaped cut-out that permits an end of the tab member to move with respect to the sidewall of the cannula.

15. The trocar cannula system of claim 14, further comprising a bend area formed in the sidewall that is configured to bias the tab member into the relaxed position wherein the tab member is positioned inwardly with respect to an outside surface of the cannula.

16. The trocar cannula system of claim 15, wherein the bend area is configured to permit selective upward deflection of the tab member, above the outside surface of the cannula, into the deformed position when the instrument is inserted into the cannula.

17. A trocar cannula system, comprising:
a cannula defined by a distal end and a proximal end; and
a medical instrument selectively insertable within the cannula;
wherein the cannula further comprises at least one tab member formed therein, each tab member being formed by a generally U-shaped cut-out in the sidewall of the cannula, and wherein the tab member further comprises crimp section that biases an end of the tab member upwardly; wherein the tab member is selectively moveable between a relaxed position and a deformed position; wherein the relaxed position is one in which the medical instrument is removed from the cannula and the end of the tab member is biased so as to be disposed below an outside surface of the cannula such that the cannula may-can be moved with respect to the tissue, and wherein the deformed position is one in which the medical instrument is inserted into the cannula and contacts the crimp section to deform the tab member and deflect the end of the tab member upwardly past the outside surface of the cannula such that the end of the tab member frictionally engages the tissue to prevent the trocar cannula from moving with respect to the tissue.

* * * * *